(12) United States Patent
Fink et al.

(10) Patent No.: US 6,778,269 B2
(45) Date of Patent: Aug. 17, 2004

(54) DETECTING ISOTOPES AND DETERMINING ISOTOPE RATIOS USING RAMAN SPECTROSCOPY

(75) Inventors: Manfred F. Fink, Austin, TX (US); Philip L. Varghese, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/234,418

(22) Filed: Sep. 3, 2002

(65) Prior Publication Data

US 2003/0053049 A1 Mar. 20, 2003

Related U.S. Application Data

(60) Provisional application No. 60/317,083, filed on Sep. 4, 2001.

(51) Int. Cl.[7] .............................. G01J 3/44; G01N 21/65
(52) U.S. Cl. ....................................................... 356/301
(58) Field of Search ......................................... 356/301

(56) References Cited

U.S. PATENT DOCUMENTS

| | | |
|---|---|---|
| 4,068,953 A | 1/1978 | Harney et al. |
| 4,953,976 A | 9/1990 | Adler-Golden et al. |
| 5,786,893 A | 7/1998 | Fink et al. |
| 6,307,626 B1 | 10/2001 | Miles et al. |

FOREIGN PATENT DOCUMENTS

EP   PCT/US02/28231    2/2003

OTHER PUBLICATIONS

Eriksen, S., New Scientist 381, 608 (1964).
Graham, D. Y., Am.J. Gastroenterol, 86, 1118 (1991).
Klein, P.D. et al., Am.J. Gastronenterol 91, 690 (1996).
Katerlaris, P.H., D.B. Jones, Am.J. Gastroenterol 92, 1245 (1997).
Logan, R.P. GUT 32, 1461 (1991).
Mansfield, C.D., H.N., Rutt, Phys. Med.Biol. 43, 1225 (1998).
Raju, G.S. et al., Am.J. Gastroenterol 89, 1027 (1994).

Primary Examiner—F. L. Evans
(74) Attorney, Agent, or Firm—Blakely, Sokoloff, Taylor & Zafman (57) ABSTRACT

The methods and apparatus described may be used for the discrimination of two closely spaced spectral lines. In certain embodiments the methods and apparatus may be used for the detection of isotopes and isotopic ratios by Raman spectroscopy. In certain embodiments the conversion of a labeled substrate to a labeled product may be detected. In particular embodiments the conversion of a $^{13}C$ labeled substrate to a $^{13}C$ labeled product may be detected. In other embodiment the conversion of $^{13}C$ urea to $^{13}CO_2$ is detected. Embodiments described include the diagnostic determination of $^{13}CO_2/^{12}CO_2$ ratio in a test sample.

29 Claims, 4 Drawing Sheets

DETECTING ISOTOPES AND DETERMINING ISOTOPE RATIOS USING RAMAN SPECTROSCOPY

CROSS REFERENCE TO RELATED APPLICATION

This application claims the benefit of U.S. provisional patent application No. 60/317,083 entitled "Detecting Isotopes and Determining Isotope Ratios Using Raman Spectroscopy," filed Sep. 4, 2001.

BACKGROUND OF THE INVENTION

1. Field of the Invention

The methods and apparatus described are related to analytical spectroscopy, in particular Raman spectroscopy. The methods and apparatus are further related to the discrimination of two closely spaced spectral lines without the use of a spectrometer. The methods are further related to the discrimination and detection of isotopes and isotope ratios using Raman spectroscopy, particularly the detection of metabolic conversion of an isotopically labeled substrate to an isotopically labeled product. In certain embodiments, a Raman shifted frequency of various gaseous compounds (such as carbon 13 labeled carbon dioxide ($^{13}CO_2$)) is distinguished from the corresponding Raman shifted frequency of the naturally abundant isotope using an atomic vapor filter. In other embodiments, a Raman shifted frequency can be employed for nitrogen 15 in $NO_x$ or $^{15}NH_3$. In one embodiment, a Raman shifted frequency can be employed for sulfur in $XSO_4$. In one embodiment, a Raman shifted frequency can be employed for deuterium in HDO or $D_2O$.

2. Background

Raman scattering is a type of inelastic scattering of electromagnetic radiation, such as visible light, discovered in 1928 by Chandrasekara Raman. If a beam of monochromatic light is passed through a substance some of the radiation will be scattered. Although most of the scattered radiation will be the same as the incident frequency (Rayleigh scattering), some will have frequencies above (anti-Stokes radiation) and below (Stokes radiation) that of the incident beam. This effect is known as Raman scattering and is due to inelastic collisions between photons and molecules leading to changes in the vibrational and rotational energy levels of the molecules. This effect is used in Raman spectroscopy for investigating the vibrational and rotational energy levels of molecules. Raman spectroscopy is the spectrophotometric detection of the inelastically scattered light.

"Stokes" emissions have lower energies (lower frequencies or a decrease in wave number ($cm^{-1}$)) than the incident laser photons. They occur when a molecule absorbs incident laser energy and relaxes into an excited rotational and/or vibrational state. Each molecular species will generate a set of characteristic Stokes lines that are displaced from the excitation frequency (Raman shifted) whose intensities are linearly proportional to the density of the species in the sample.

"Anti-Stokes" emissions have higher frequencies than the incident laser photons. Anti-Stokes emissions occur only when the photon encounters a molecule that, for instance, is initially in a vibrationally excited state due to elevated sample temperature. When the final molecular state has lower energy than the initial state, the scattered photon has the energy of the incident photon plus the difference in energy between the molecule's original and final states. Like Stokes emissions, anti-Stokes emissions provide a quantitative fingerprint for the molecule involved in the scattering process. This part of the spectrum is seldom used for analytical purposes since the spectral features are weaker. However, the ratio of the Stokes to the anti-Stokes scattering can be used to determine the sample temperature if it is in thermal equilibrium.

The Stokes and anti-Stokes emissions are collectively referred to as spontaneous "Raman" emissions. Since the excitation frequency and the frequency of the Stokes (and anti-Stokes) scattered light are typically far off the resonance of any component in the sample, fluorescence at frequencies of interest is minimal. The sample is optically thin and will not alter the intensities of the Stokes emissions (no primary or secondary extinctions), in stark contrast to infrared spectroscopy.

Spectroscopy may be used in a variety of diagnostic tests, in particular diagnosis of Helicobacter pylori (H. pylori) infection. H. pylori is a spiral shaped bacterium that lives in the stomach and duodenum, a section of intestine just below stomach. It has a unique way of adapting to the harsh environment of the stomach. The inside of the stomach is bathed in about half a gallon of gastric juice every day. Gastric juice is composed of digestive enzymes and concentrated hydrochloric acid, which can readily tear apart the toughest food or microorganism. The stomach is protected from its own gastric juice by a thick layer of mucus that covers the stomach lining. H. pylori take advantage of this protection by living in the mucus lining and counteracting a local acidic environment with the enzyme urease. Urease converts urea into the acid neutralizing compounds bicarbonate and ammonia. The production of these acid-neutralizing chemicals around H. pylori protect it from the acid environment of the stomach.

H. pylori are isolated from the body's immune response by the mucus lining of the stomach. The immune system will respond to an H. pylori infection by sending cellular mediators of the immune response and other infection fighting agents. However, the mucus lining of the stomach is not readily accessible to cellular mediators of the immune response. As long as the bacteria are present the immune system continues to respond. Cellular mediators of the immune response die and release superoxide radicals and similar compounds on the cells of the stomach lining. H. pylori can feed on the extra nutrients that are sent to reinforce the cellular mediators of the immune response and within a few days gastritis results, and perhaps eventually a peptic ulcer. It may not be H. pylori itself which causes the peptic ulcer, but the inflammation of the stomach lining; i.e. the response to H. pylori.

Traditionally endoscopy with biopsy is used to check for ulcers, but recently, non-invasive methods have been developed for detecting H. pylori. Certain conditions and diseases, including H. pylori infection, can be detected non-invasively by analyzing the conversion of a labeled substrate into a labeled product. For instance, air exhaled by persons suspected to be infected by H. pylori can be analyzed to detect the presence of the bacteria in the gastrointestinal tract. In one such method, a patient swallows a radiolabeled urea preparation, $^{14}C$ labeled urea. H. pylori present in the gastrointestinal tract degrade the urea to ammonia and bicarbonate, the bicarbonate being labeled with $^{14}C$. The gastrointestinally formed bicarbonate is converted to $^{14}C$ labeled carbon dioxide and is transported to the lungs through the normal physiology of the body where it is exhaled together with carbon dioxide formed by other body processes. In one detection method the exhaled carbon dioxide ($CO_2$) is trapped and examined with a scintillation counter to detect the presence of $^{14}CO_2$ by radioactive decay. A similar method uses the ingestion of $^{13}C$ labeled urea and a combination of gas chromatography/mass spectroscopy to detect $^{13}CO_2$ in the breath. In another method of detection infrared spectroscopy is used to detect $^{13}CO_2$ in the breath.

Current techniques available to the physician for the detection of H. pylori by a breath test are scintillation counting of $^{14}CO_2$ in breath samples and mass spectrometric analysis of $^{13}CO_2$ in breath samples analyzed by an off-site central laboratory. These techniques require about one week for analysis. The use of $^{14}C$ typically requires the presence of a physician trained in nuclear medicine and can not be used in pregnant women and children, as well as being banned in countries such as Sweden and France. These methods entail the submission of a sample to an offsite laboratory, and/or the handling of radioactive materials, which is both time consuming and expensive.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

In particular embodiments two closely spaced spectral lines may be differentiated by the use of an atomic vapor filter, preferably a cesium vapor filter. A laser source may be tuned to an appropriate frequency such that one of two spectral lines is coincident with the absorption frequency of an atomic vapor filter. The frequency of a laser source may be altered so that the spectral line coincident with an atomic vapor filter may shift from within to outside of the absorption window of an atomic vapor filter. The difference of signal intensity between the two states, derived from the initial and shifted laser frequency, in conjunction with the intensity detected when the frequency of the first spectral line is coincident with absorption frequency of an atomic vapor filter allows one to determine the ratio of the two spectral lines. The discrimination of two closely spaced spectral lines allows the ratio of the molecular species represented by the spectral lines to be determined. In one embodiment, spontaneous Raman spectroscopy is employed. While described with reference to isotope ratios for carbon dioxide, embodiments of the invention are not so limited, as embodiments of the invention can be used in conjunction with other types of compounds. For example, embodiments can be used to differentiate and determine isotope ratios for compounds such as nitrogen, hydrogen, sulfur, etc.

Embodied methods include the introduction of an isotope labeled substrate into an environment where a substrate may be converted to a labeled product. The labeled product can be in a gas, liquid, or solid form and a component of a gas, liquid, or solid sample. A labeled product can be detected using a modified Raman spectrometer, as described below. In certain embodiments the ratio of labeled product to a non-labeled product can be determined. In particular an alteration in an isotopic ratio between a standard and an experimental sample may be indicative of the conversion of a labeled substrate to a labeled product. In certain embodiments the absence of a change in an isotopic ratio can be indicative of a malfunctioning organ or body system. In other embodiments a change in an isotopic ratio can be indicative of the presence of a pathogen. A standard sample may be a sample taken prior to labeled substrate administration (baseline) or an artificial sample with known amounts of a compound representative of the labeled product. An experimental sample can be a sample taken at an appropriate time(s) after administration of a labeled substrate.

In an embodiment, an isotope labeled substrate may be converted to a labeled product by a metabolic process. In particular embodiments, the metabolic process can be associated with a disease state. The disease state may be the result of a pathogen or an abnormal physiology. In a particular embodiment, the labeled substrate may be converted to isotopically labeled products, for example carbon-13 labeled $CO_2$ ($^{13}CO_2$), which is processed by the body and exhaled in the breath. The breath may be sampled discontinuously or continuously. In another embodiment, nitrogen-15 labeled substrates can cause the body to generate and exhale through the breath $NH_3$.

In certain embodiments the intensity of the $^{13}CO_2$ Raman shift of 1370.08 $cm^{-1}$ can be detected by selective absorbance of the $^{12}CO_2$ Raman shift of 1388.2 $cm^{-1}$. The ratio of $^{13}CO_2$ to $^{12}CO_2$ can be determined by shifting the frequency of the light source slightly to allow the passage of both Raman lines from which the difference between the frequency shifted light source and the initial light source is used to determine the ratio of the intensities of the $CO_2$ Raman lines.

Figure 1:
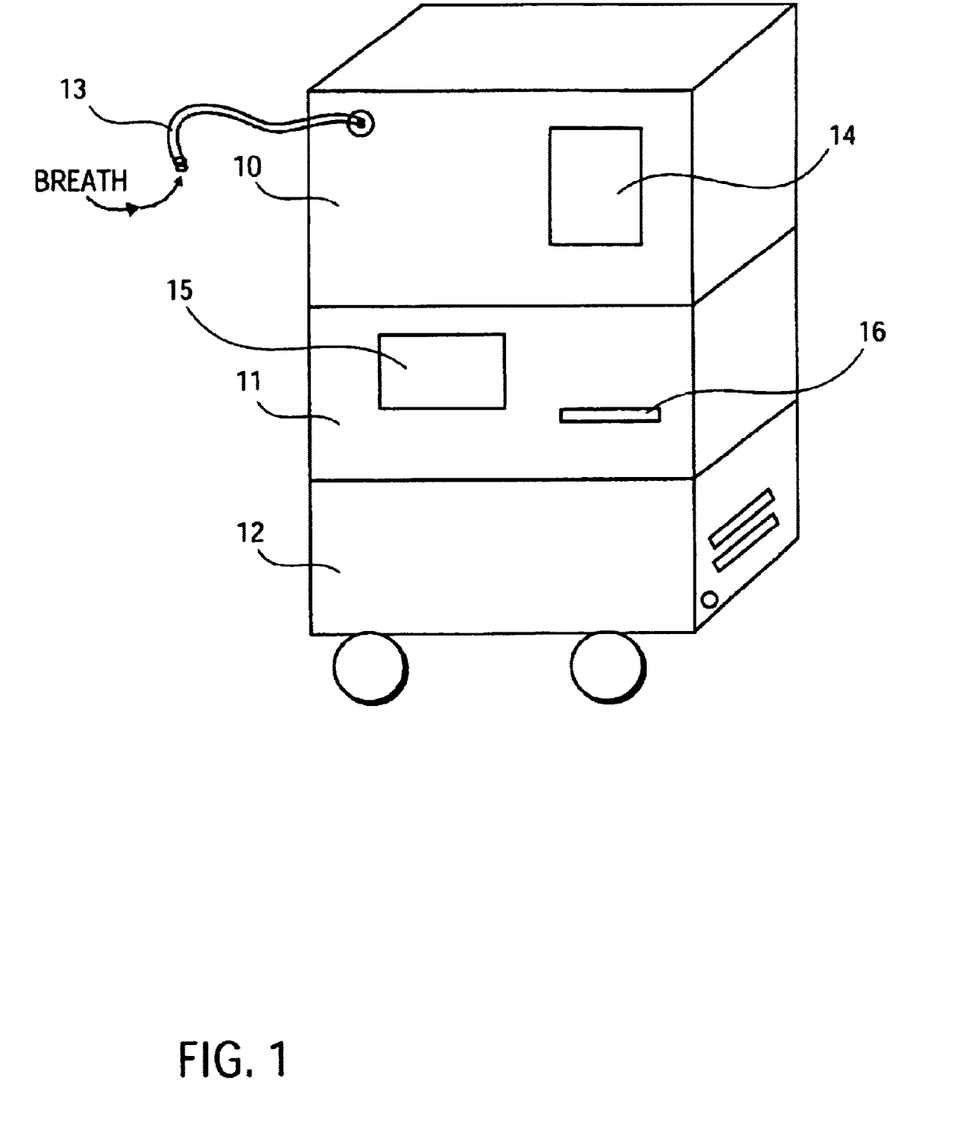
FIG. 1 illustrates a system incorporating a Raman spectrometer for on-site determination of the isotopic composition of breath samples, according to one embodiments of the invention.

FIG. 1 illustrates a system incorporating a Raman spectrometer for on-site determination of the isotopic composition of breath samples, according to one embodiments of the invention. FIG. 1 illustrates a system comprising a Raman spectrometer 10, a data processing system 11, and a power supply 12. A breath collection tube 13 is operatively connected to the Raman spectrometer 10. A breath collection tube 13 will provide for a breath sample to be taken and introduced into a sample cell within the spectrometer 10. Sample cells for the collection of breath are known to the artisan. Preferably, a breath sample will be obtained through the nasal passages of a patient. An instrumentation panel 14 is also operatively connected to the Raman spectrometer 10. An instrument panel 14 may provide for operation of the spectrometer including calibration and adjustment. A data processing unit 11 may be incorporated into the system. The data processing unit 11 will receive data from the Raman spectrometer and process the data to be displayed in an appropriate format on a monitor 15 and/or by printing on a printer 16. The breath analysis system will incorporate an appropriate power supply 12 operatively connected to the system.

The data processing unit 11 includes memories, processors and/or Application Specific Integrated Circuits (ASICs). Such memory includes a machine-readable medium on which is stored a set of instructions (i.e., software) embodying any one, or all, of the methodologies described herein. Software can reside, completely or at least partially, within this memory and/or within the processor and/or ASICs. For the purposes of this specification, the term "machine-readable medium" shall be taken to include any mechanism that provides (i.e., stores and/or transmits) information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

Figure 2:
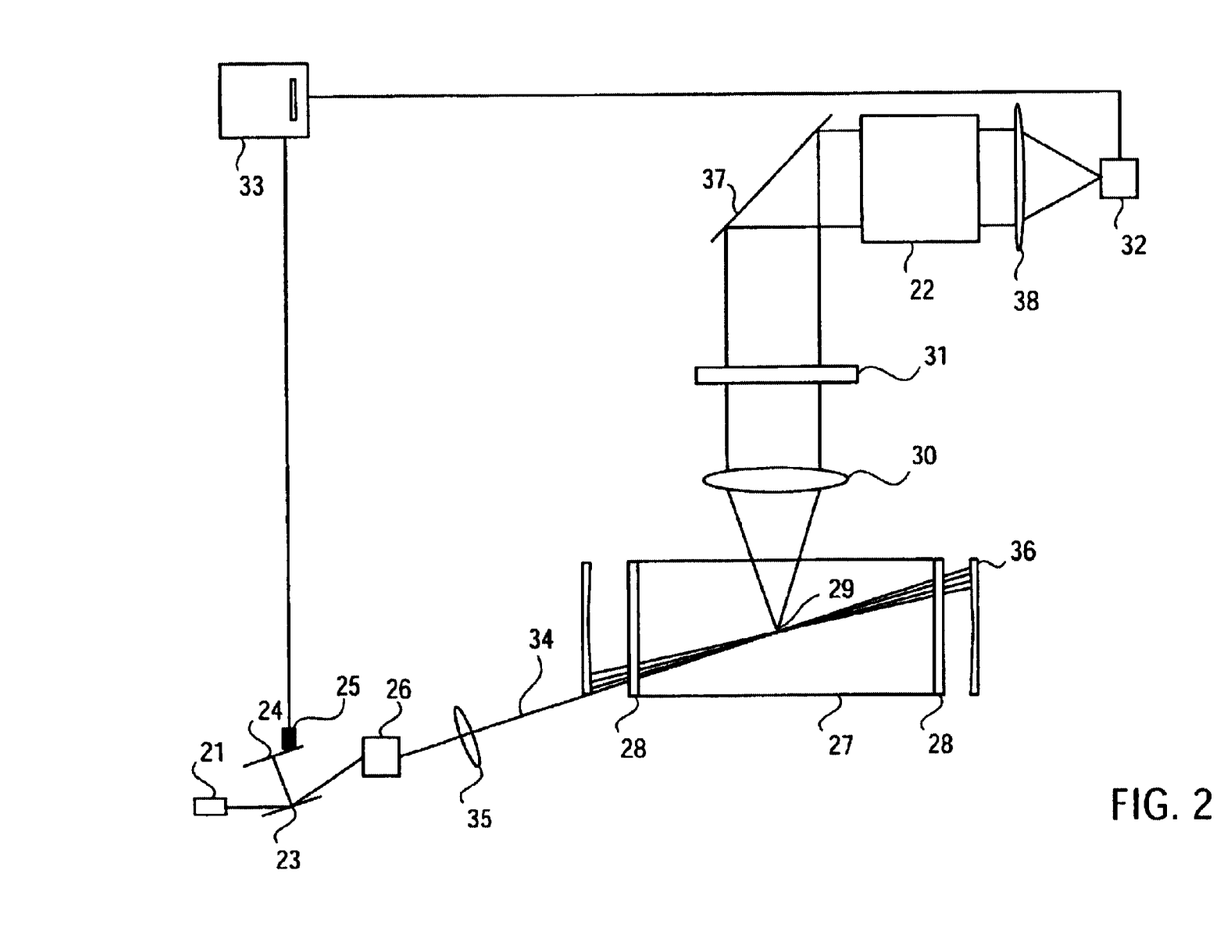
FIG. 2 illustrates a Raman spectrometer, according to one embodiment of the invention.

FIG. 2 illustrates a Raman spectrometer, according to one embodiment of the invention. FIG. 2 diagrams an embodiment of an apparatus used to detect a $^{13}CO_2/^{12}CO_2$ ratio in the breath of a patient. In one embodiment the apparatus is designed to eliminate the passage of a $^{12}C$ line that is shifted 1388.2 cm$^{-1}$ from a laser diode or monochromatic light source 21 at 12,574 cm$^{-1}$. (795 nm) The resonance of a cesium (Cs) vapor filter 22 is 894 nm or 11,186 cm$^{-1}$. The illustrated apparatus comprises arrangement of optical elements that can be used to detect the isotope ratio in breath, particularly $^{13}C$ and $^{12}C$. Laser diode 21, grating 23, mirror 24, and piezo 25 produce an intense, monochromatic laser beam 34 with a wavelength stability that can be better than 400 MHz. The laser optics 26 comprises a chopper and polarization rotator (half-wave plate) to record two spectra with orthogonal polarization. The difference of these measurements will isolate the Q-branches of the spectrum, removing all the small rotational sidebands at the base line. The laser beam is focused through a focusing lens 35 into the gas cell 27 with double sided anti-reflection coated windows 28 to allow multi-pass operation in a multi-pass cavity 36. Gas cell 27 can receive the air exhaled by a patient where it will be exposed to the laser beam 34. The light scattered at the focal point 29 in the gas cell may be collected by an achromat 30 which illuminates a narrow band pass filter 31 (2±0.4 nm), centered on the line of the $^{13}CO_2$ dyad at 1370.08 cm$^{-1}$ from the laser energy. The light is reflected by mirror 37 crossing through a Cs cell 22 that can further reduce the light passing the filter. The Cs cell 22 can remove the $^{12}C$ line at 1388.20 cm$^{-1}$ of the $CO_2$ dyad with very high efficiency (60 db).

Figure 4:
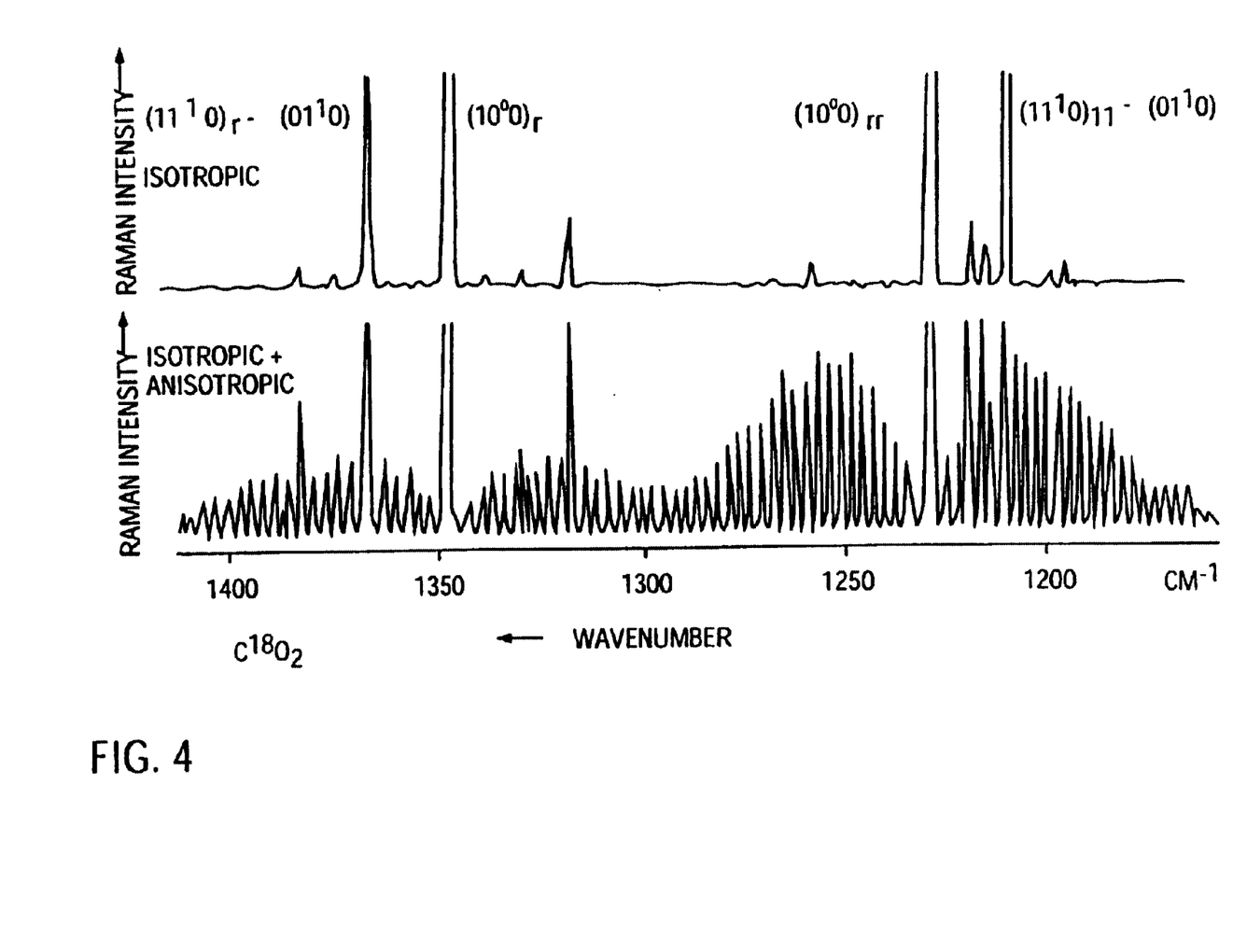
FIG. 4 illustrates an example of a separation of the rotational sidebands from a signal by using a chopper and polarizer, according to one embodiment of the invention.

The laser frequency is set 1388.2 cm$^{-1}$ from the resonance of the Cs cell 22 (11,177.8 cm$^{-1}$ or 894 nm), which is 12,574 cm$^{-1}$ (corresponding wavelength 795 nm). At this laser frequency (12,574 cm$^{-1}$) the Cs cell 22 of FIG. 2 will absorb the light Raman shifted by 1388.2 cm$^{-1}$, independent of angles and polarization. The transmitted spectrum is a $^{13}CO_2$ line at 1370.08 cm$^{-1}$ and some rotational sidebands. These two components can finally be separated by the polarization recordings since the rotational transitions are non-polarized while the Q-branch lines are polarized. The Q-branch arises from photon emission related to pure vibrational transitions in which there is a change in vibrational energy but no change in rotational energy. The surviving photons will be passed through a focusing mirror 38, detected with an avalanche photo-diode 32, and recorded in a computer system 33. FIG. 4 illustrates an example of a separation of the rotational sidebands from a signal by using a chopper and polarizer, according to one embodiment of the invention. The comparison of spectra with orthogonal polarization can be used to separate the Q-lines of a spectrum. FIG. 4 is the spectrum of $C^{18}O_2$ and is exemplary of $^{13}CO_2$ and $CO_2$ spectra.

Figure 3:
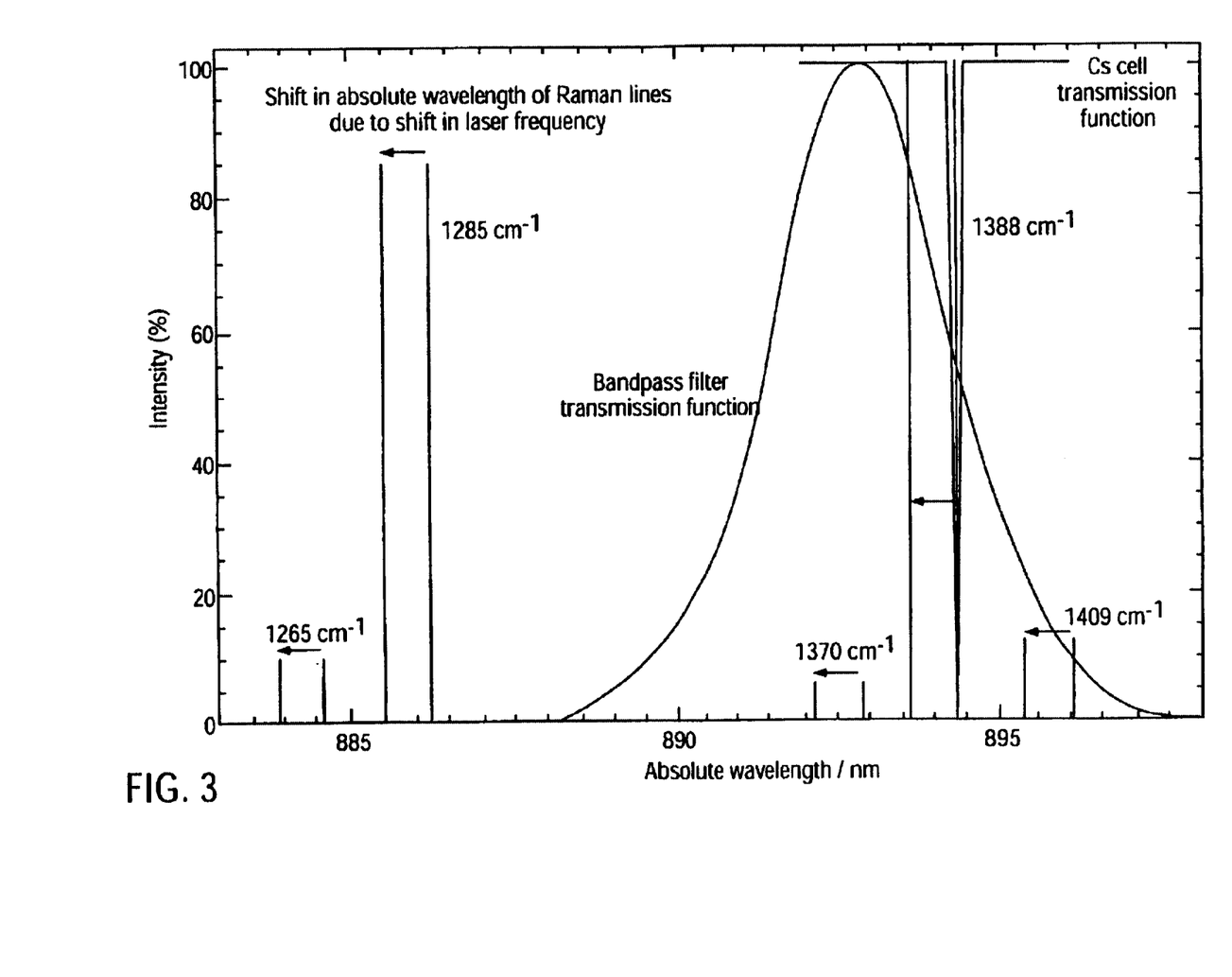
FIG. 3 illustrates an example of a Cs vapor and bandpass filter absorption profile with Raman spectrum at two excitation frequencies superimposed on the profile, according to one embodiment of the invention.

In order to measure the ratio of $^{13}CO_2$ and $^{12}CO_2$ the laser frequency can be shifted, preferably by 9 cm$^{-1}$. The laser frequency may be shifted with a slight tilt of the mirror 24 with a Piezo-crystal 25 or by other methods known in the art. After a shift in the laser frequency, the Cs cell 22 illustrated in FIG. 2 will pass both Raman lines for $^{12}CO_2$ and $^{13}CO_2$, (1388.2 cm$^{-1}$ and 1370.08 cm$^{-1}$, respectively) and the difference between the Raman intensity with initial laser frequency and the Raman intensity of the shifted laser frequency can be used to determine the intensity of the 1388.2 cm$^{-1}$ $^{12}CO_2$ Raman line and the $^{13}CO_2$ at 1370.08 cm$^{-1}$. FIG. 3 illustrates an example of a Cs vapor and bandpass filter absorption profile with Raman spectrum at two excitation frequencies superimposed on the profile, according to one embodiment of the invention. At a first excitation frequency a Raman line of $CO_2$ at 1388.2 cm$^{-1}$ is coincident with the absorption of the Cs vapor filter (Cs cell transmission function). The line representing the Cs cell transmission function depicts the absoption (intensity tending towards 0%) at a particular wavelength, 1388 cm$^{-1}$. The bandpass filter transmission function illustrated in FIG. 3 depicts an effect of a bandpass filter that only allows the passage of light within the frequencies of interest. Also illustrated in FIG. 3 is a shift in Raman lines due to a shift in excitation frequency, Raman lines associated with a first excitation frequency in closed bars and Raman lines associated with a second excitation frequency in open bars. The x-axis is the absolute wavelength in cm$^{-1}$ and the y-axis is percent intensity of light. A $^{13}CO_2$ line can be seen at a Raman shift of 1370.08 cm$^{-1}$ at the initial excitation frequency. Also depicted is a $^{12}CO_2$ Raman shift at 1388.2 cm$^{-1}$, as well as 1265 cm$^{-1}$ 1285 cm$^{-1}$ and 1409.5 cm$^{-1}$ at the initial excitation frequency The apparatus described may absorb the 1388.2 cm$^{-1}$ Raman line by using a laser source that typically is 1388.2 cm$^{-1}$ greater than the absorption resonance of a Cs cell vapor filter, thus the resonance of the Cs vapor would coincide with a Raman shift of $^{12}CO_2$ and the Raman shift at 1370.08 cm$^{-1}$ may be evaluated. Excitation at a second excitation frequency shifts the 1388.08 cm$^{-1}$ to a lower wavelength so that it is not coincident with the Cs cell transmission function. The ratio of the intensities at the two excitation frequencies may be used to determine the ration of the $CO_2$ isotopes in a sample.

In one embodiment, the optical setup of the spectrometer may be that described below. The laser diode used (SDL-2369-P1, output power 1.2 W, single emitter) may be passively locked into single-mode operation, with a bandwidth of less than 500 MHz, by an external cavity arrangement using a high-quality diffraction grating in Littman-Metcalf configuration. Simple beam shaping optics allow correction of astigmatic focusing of the beam, so that 300 mW of light is sent into a multi-passing cavity inside the sample chamber of the spectrometer. The laser is tuned to a frequency that is sum of the $D_1$ absorption line of Cs and the Raman shift of a target molecule, so that glass cells containing this metal can be used as narrow-band width notch filters for suppression of a Raman shifted spectral line of a target molecule.

In certain embodiments, the collection optics may be used in a standard right angle scheme, and by using a feedback mirror a solid angle of collection $\Omega=0.7$ sr may be obtained; the optical system, composed of two lenses, may have a magnification factor, M=4, sending the collected light into a single grating spectrometer (adapted from a SPEX Triplemate, Model No. 1877, f/#7). The spectral resolution depends on the grating and the slit width used: 1 cm$^{-1}$ for a 1200 grooves/mm grating, with 20 μm slit width; and 5 cm$^{-1}$ for a 600 grooves/mm grating with 50 μm slits. A dove prism may be placed in front of the spectrometer slit in order to tilt the image by 90° thus maximizing the Raman signal collection.

Isotope ratios can be measured, as well as or even more accurately, with a modified Raman spectrometer, an example of which is illustrated in FIG. 2. A Raman spectrometer, as described above, may be modified to provide an apparatus for the detection of isotopes and isotopic ratios. The apparatus can be designed so that a small and inexpensive apparatus can be used in a physician's office, such as a gastroenterologist. The apparatus can be sized so that it is easily stored until it is needed and portable so that it may be moved when appropriate. The operation of the apparatus can be simple and straightforward, such an instrument can be operated with a minimum of training. Certain embodiments of the apparatus may be designed for operation by a nurse or office personnel. Data may be made available immediately and a physician can diagnosis, monitor, and/or treat a patient in a cost effective and timely manner. The use of the narrow line width of the Cs absorption filter to absorb the Raman line at 1388.2 cm$^{-1}$ is a unique feature of the methods and apparatus described. Another unique feature is the polarization analysis in combination with the Cs cell absorption in the recordings of Raman spectra, a technique unique in medical analysis.

Testing for Substrate Conversion

In certain embodiments, the described Raman spectrometer may be used to non-invasively test for the conversion of an isotopically labeled substrate by analysis of a sample, in particular a breath sample. Standard testing for the conversion of an isotope labeled substrate to a labeled product typically relies on the collection of breath samples in a balloon or similar device and the processing of the samples in an off-site laboratory. A particular advantage of the methods and apparatus described is that a Raman spectrometer can be used for on-site testing and results can be obtained within approximately an hour after testing is completed, without the use of radioactive substances.

Certain embodiments provide the physician with a quick and inexpensive method to diagnose his patients without multiple visits and without specially trained colleagues. In addition to the time and cost advantages, a series of measurements over several weeks can be obtained by embodied methods so that a doctor can follow the patient's recovery or lack thereof, and adjust or change the medicine according to the patient's needs. The methods and apparatus described may reduce the need for a return visit by a patient for discussion of results, further testing or re-testing, and/or altering a treatment program. The methods and apparatus can provide an analysis which records the presence of a pathogen or the malfunction of an organ with an instrument which is affordable, can be run by a nurse, requires no radioactive substances and will do so with the required precision. With this tool at hand, the physician can diagnose a patient in a timely manner, start treatment, and follow the healing process, while making adjustments as needed.

In certain embodiments of the invention, the breath sample is deposited directly into a Raman spectroscopy apparatus, bypassing the need to collect a breath sample in a balloon or similar device and to transfer a sample to a laboratory, or the like, for analysis. Also, the time it takes for results to be communicated to the physician from the off-site laboratory is circumvented with the described methods and apparatus.

In an embodiment an isotope labeled urea ($^{13}CO(NH_2)_2$) molecule can be introduced into a body, preferably by mouth, to test for the presence of a pathogenic bacteria, such as *H. pylori*. The isotope labeled urea can be metabolized by *H. pylori* to a yield the isotopically labeled product (bicarbonate) that can be converted to isotopically labeled carbon dioxide, ($CO_2$) by inherent body processes. Isotopically labeled $CO_2$ is subsequently exhaled in the breath. The test typically comprises sampling a patient's breath before and after administering isotopically labeled urea and determining by Raman spectroscopy the ratio between labeled and non-labeled $CO_2$. The reaction of urea hydrolysis in which urea is broken down to ammonia and carbon dioxide is shown below. Reaction 1 is important for diagnosis of *H. pylori* by a breath test.

(1)

The bicarbonate is neutralized and the resulting carbonate can be reversibly converted to water and carbon dioxide, as illustrated in reaction 2.

(2)

In general, a healthy person will show the natural abundance of 100:1.1 in favor of $^{12}C$. However, if a patient has ulcers or gastritis that may develop into ulcers then *H. Pylori* may be present in the gastrointestinal tract. *H. pylori* metabolizes urea leading to an about ten percent increase of the carbon dioxide in the breath. In order to label the $CO_2$ generated in the stomach, the administered urea can be enriched to approximately 99.7% with the isotope $^{13}C$. Therefore the exhaled breath has about a 10 times higher concentration of $^{13}CO_2$ than the breath of a healthy person.

Alternative Embodiments

The described methods are not limited to analysis of the conversion of a labeled urea to labeled $CO_2$. Alternative embodiments may use the conversion of other $^{13}C$ labeled substrates in the isotopic analysis of $CO_2$. These methods are based on a $^{13}C$ enriched substrates that may be converted to a labeled product, in particular an organ or organ system may be tested. A diseased organ may include a damaged organ, functional disorder or an infection with a pathogen such as a parasite, virus, or bacteria. In one embodiment, the appearance of $^{13}CO_2$ indicates that a substrate has been converted into its products. Conversion of the substrate typically indicates that either a normal bodily process is converting a substrate, indicating the proper functioning of the body. Thus, if the body fails to convert the substrate then the body function is faulty. Alternatively, a substrate that may normally not converted by the body, but is being converted may be indicative of a pathogen.

Other alternative embodiments can contribute to the advancement of other biomedical diagnostic methods. Breath tests are highly reliable and non-intrusive, making them appropriate for a diversity of biological processes. Examples include, but are not limited to drug metabolism, liver disease investigations, and metabolic investigations. For, example Midazolam is a sedative and amnesic medication that is extensively metabolized in the liver by the CYP3A4 enzyme. $^{14}C$-erythromycin breath tests (ERMBT) are used to detect the efficiency of midazolam metabolism in the liver. An alternative embodiment is the detection of the metabolism of $^{13}C$-erythromycin using breath analysis methods described.

Both $^{13}$C-aminopyrine and $^{13}$C-methacetin breath tests can be used in the diagnosis of liver damage. With the $^{13}$C-aminopyrine breath test (ABT) it is possible to monitor the decline of liver function over time.

Pancreatic amylase is the major enzyme involved in the hydrolysis of starch. $^{13}$C-starch can be hydrolyzed into glucose and the excess is expelled and measured in the feces, yielding information on the digestion of starch and its metabolic use. One embodiment can be the detection of decreased activity of pancreatic amylase in children with cystic fibrosis.

Digestive Microbiology

Currently, one of the most widely used breath test in the world is the $^{13}$C-urea breath test for the diagnosis of *H. pylori* infection. The principle of the test relies on the urease activity of *H. pylori*, as described above, which transforms $^{13}$C-urea given by mouth (75 to 100 mg for adults, 50 mg for children) into ammonia and $^{13}$CO$_2$. Two breath samples may be obtained, one before the administration of urea (T$_0$), and the second 30 minutes later (T$_{30}$). The result of the test may be expressed as the difference of isotopic enrichment between T$_{30}$ and T$_0$. The urea breath test may be performed after a 6-hour fast. Several solutions may be used to slow down gastric emptying of urea and optimize the results of the test: citric acid is one choice (200 ml at 0.1 N) (Graham et al., 1999).

The sensitivity and specificity of the breath test can be >95%, compared to the direct diagnosis on gastric biopsies by histology or culture, for the initial diagnosis of the infection as well as for the control of eradication.

The urea breath test does not require an endoscopy, and may give a clear positive or negative answer. The urea breath test may be performed at least 4 weeks after the end of the antibiotic treatment. It is also probably better (but not essential) to stop anti-secretory drugs before the test, especially for some drugs that have a urease inhibitory effect.

The diagnosis of small bowel bacterial overgrowth in the presence of chronic diarrhea or recurrent abdominal pain may be performed by a glucose/hydrogen breath test. Glucose is easily absorbed by the intestinal epithelium; an increase of breath hydrogen after glucose ingestion corresponds to a digestive fermentation of glucose prior to its absorption, and thus to the presence in excess of bacteria in the small bowel. $^{13}$C-xylose and $^{13}$C-glycocholic acid (conjugated bile salt) have also been used to detect bacterial overgrowth.

Digestive Motility

The $^{13}$C-octanoic acid breath test described by Ghoos et al., 1993 allows the measurement, with a precision comparable to scintigraphy, of the gastric emptying of solids. Its simplicity, low cost and absence of radioactivity should favor this test compared to scintigraphic methods. The main indications of this test are the diagnosis of gastroparesis in case of unbalanced diabetes mellitus, and the investigation of dyspeptic syndromes especially after gastro-esophageal surgery.

The oro-caecal transit time (OCTT) can be measured by a lactose-$^{13}$C-ureide breath test. These two non-absorbable molecules are metabolized by the bacterial flora of the colon, converting lactose-$^{13}$C-ureide to $^{13}$CO$_2$. The delay between the oral administration of the substrate and the appearance of $^{13}$CO$_2$ in breath corresponds to the OTTC.

Exploration of Lactose Digestion

Lactose intolerance is frequently suspected in children and adults with diarrhea and abdominal pain promoted by the ingestion of milk products. A $^{13}$C-lactose breath test may allow the indirect and non-invasive detection of lactase deficiency, which is associated with a decreased $^{13}$CO$_2$ production. The measurement of both hydrogen and $^{13}$CO$_2$ after administration of $^{13}$C-lactose may improve the sensitivity of this breath test.

Exocrine Pancreatic Function

Several tests with $^{13}$C-labeled substrates have been described for the investigation of exocrine pancreatic function. The orally administered molecules (triglycerides, triolein, . . . ) are substrates for the different pancreatic enzymes. $^{13}$CO$_2$ production may be correlated to the enzymatic activity present in the gut. These tests are used mainly for the diagnosis and follow-up of patients with chronic pancreatitis or cystic fibrosis. Their efficacy is similar to the measurement of the fecal fat output or the enzymatic activities (such as elastase) in stools.

Dynamic Liver Function Tests

Numerous breath tests are known that correspond to a multiplicity of liver functions. Depending on the liver diseases studied, these tests may yield quantitative information on a given metabolic pathway. Three groups of substrates can be defined, allowing the exploration of:

a) liver cytosolic enzymes, b) cytochrome P450 activities (microsomal enzymes), and c) mitochondrial enzymatic pathways.

$^{13}$C-galactose or $^{13}$C-phenylalanine, substrates of cytosolic enzymes, can be markers of liver function mass, because their metabolism is relatively independent of induction or inhibition interactions. The repetition of these breath tests over time in a patient with chronic liver disease (viral hepatitis, alcoholic cirrhosis, primary biliary cirrhosis) may indicate an evolution towards hepato-cellular insufficiency (Reichen et al., 1991 and Merkel et al., 1996). A correlation between the results of the $^{13}$C-galactose breath test and the severity of fibrosis in patients with chronic hepatitis C has been shown (Mion et al., 1999).

Cytochrome P450 substrates (such as $^{13}$C-aminopyrine, $^{13}$C-caffeine, $^{13}$C-erythromycin) allow the determination of individual phenotype of these enzymatic activities in a given population. Drug interactions can be studied by using breath tests (Rost et al., 1992). The quantitative evaluation of liver function mass is also possible (Mion et al., 1995).

Finally, $^{13}$C-keto-isocaproic acid, an analog of leucin, or $^{13}$C-octanoic acid has been used as non-invasive markers of hepatic mitochrondrial functions. For example, $^{13}$C-keto-isocaproic breath test allows the distinction between alcoholic steatosis and non-alcoholic metabolic fatty liver (secondary to diabetes mellitus or obesity) (Mion et al., 1995).

Certain embodiments are non-invasive methods for the functional assessment of an inherited metabolic disorder in which the whole-body galactose oxidation capacity is measured by the described methods using $^{13}$C-galactose as a substrate, to identify infants at highest risk from continued galactose consumption. Newborn infants may be routinely screened for the presence of inherited metabolic disorders. These disorders are the consequence of a gene mutation that alters or inactivates a key enzyme in the metabolism of a nutrient such as a carbohydrate or amino acid. One of the most common of such disorders is galactosemia, which occurs in 1 of every 8700 live births. Classical galactosemia is a potentially lethal disease caused by mutations that impair galactose-1-phosphate uridyl-transferase (GALT) (enzyme classification 2.7.7.12). This enzyme catalyzes the second step in the critical metabolic sequences, which convert galactose to glucose. Since the newborn infant's principle nutritional energy source is lactose (disaccharide of glucose and galactose), this pathway is critical both for energy from glucose-1-phosphate oxidation and for uridyl diphosphate-galactose as a source for posttranslational galactosylation of membrane proteins in the rapidly growing infant.

Deficiency can lead to catastrophic events in the newborn with symptoms progressing from poor feeding, prolonged jaundice, bleeding diathesis and cataracts to E. coli sepsis and death. The simple exclusion of galactose from the newborn diet halts this toxic progression and is lifesaving. One may anticipate that the sooner in the newborn's life the diagnosis is suspected and the dietary change to sucrose-based (soy) formula is made, the better the short-term outcome in preventing neonatal death.

At present, newborn screening is carried out for GALT using enzyme linked methods on blood samples obtained by heel stick and blotted on filter paper. This process measures enzyme activity in the red blood cell that is non-nucleated and possesses no protein synthesis capability. If the GALT enzyme is destabilized by a mutation or is inactivated by high environmental temperatures during transport of the sample, it will result in return of a positive galactosemic result even if clinically significant amounts of GALT are present. Follow-up screening by biochemical phenotyping and molecular genotyping are then required to characterize the positive screening result.

An exemplary method of a breath test, in particular a screen for GALT, is as follows. A patient must appear for diagnostics while fasting for 6 hours and has not taken antibiotic medicine that may disrupt the functioning of the bacteria. In order to avoid coating of our windows with exhaled water the breath is collected through the nose. The whole Raman spectroscopy unit is kept at 40° C. or 105 F. The Raman spectroscopy unit is calibrated once a day, which can be done with the carbon dioxide in ambient air. The Raman spectroscopy unit is operatively connected to line power and is designed to make the instrument portable.

Collection of Baseline Breath Sample.

A sample of end-tidal air is collected from a patient. For newborn infants, the preferred collection method includes the breath collection device equipped with a neonatal resuscitation mask with a one-way inlet valve. Exhaled breath is collected in the Raman spectroscopy sample cell, preferably 5 ml in volume.

Administration of Test Substrate:

The substrate may include $^{13}$C-galactose and is administered to a patient in a dosage of approximately 5 mg per kg subject body weight by an oral or intravenous route.

Collection of Post-dose Breath Samples

Using the techniques described above, serial breath sample(s) are collected at approximately 10 to 30 minutes. After which analysis of $^{13}$C isotopic abundance of $^{13}CO_2$ of breath samples is performed. The breath samples are analyzed for the isotopic abundance of $^{13}CO_2$ ($^{13}CO_2/^{12}CO_2$), by Raman spectrometry.

In alternative embodiments the conversion of other labeled substrates to labeled products can be calculated and the difference in the ratio of labeled product to non-labeled product can be used to determine the presence of a pathogen or the proper functioning of organs or organ systems. Essentially any metabolic conversion of a labeled substrate that results in the production of $CO_2$ can be detected by the embodied methods. In addition to $CO_2$, other labeled products may be detected (such as NO with $^{15}$N and $^{18}$O) and in samples such as breath, urine, blood, stool, body fluids or tissues of a patient. The labeled products are not limited $^{13}$C labeled products. Other isotopes can used to label substrates, such as $^{15}$N, $^{18}$O, and other stable isotopes.

Alternatively the labeled substrate may be exposed to an environment such that the molecule is converted to a labeled product by a thermal, chemical, catalytic, and/or electrochemical process. As an non-limiting example, $^{13}$C labeled oil or fuel for testing the efficiency or integrity of an engine.

In other alternative embodiments the methods can be used to analyze samples from oxidation processes in open systems like engines, or during chemical reactions. By selected exposure of the process to an isotope labeled substrate the history of this compound can be analyzed by taking samples of the air, fuel, and/or lubricant of the system and testing them with described methods.

Raman Spectrometer

A Raman spectrometer may be adapted to rapidly analyze most any gas mixture or other sample. An incident laser source for a Raman spectrometer may include four one-Watt laser diode arrays that are injection locked by a master oscillator. In one embodiment, the oscillator may be set to correspond to a resonance equal to the frequency of a target molecule Raman shift added to the frequency of an atomic vapor $D_1$ transition. It is known that the high monochromaticity of master oscillator (better than 30 MHz) can be fully transferred to a diode array and maintained for any desired length of time (Wang, et al., Optics Letters, Vol. 17, p. 1593 (1992); Yu, et al., J. Phys III France, Vol 2, p. 1615-22 (1992)). A master oscillator may be protected from optical feedback by an optical isolator. This may be done with an optical isolator based on the Faraday effect in a crystal with a large Verdet constant (available, for example, from Isowave in New Jersey, Model I-80U4). Suitable laser diode arrays are offered by Spectra Diode Labs, San Jose, Calif. (for example, the SDL-2400 Series). A suitable master oscillator may be a Series SDL-5400, also from Spectra Diode Labs.

A laser diode array may be made monochromatic by various means, such as injection locking by a single mode master oscillator, by self injection locking in a ring arrangement, by self-injection locking in a grating feedback tuned arrangement or by use as an amplifier of a single mode master laser. All of these techniques are included when the term "injection-locked" is used herein.

Diode arrays may be mounted at four corners of a multi-pass cell comprising mirrors that are so chosen and arranged so that they reflect the laser light a plurality of times and form a common focal region. A combined laser power of about 400 W may be attained, having the frequency and monochromaticity of the master oscillator. Similar multi-pass cells have been utilized for some time with single laser beams (J. C. Robinson, et al., Rev. Sci. Instr., Vol. 63, p. 3280-84 (1992)). The multi-pass cell includes two concave mirrors whose focal region is close to half the distance between the mirrors (the focal points of the mirrors are not precisely coincident, and therefore the term "focal region" is used). The mirrors may be coated with dielectric layers to give reflection coefficients of up to 0.9999. This may minimize the production of stray light and the absorption in the surface, and it will return the laser light substantially unattenuated for the remaining reflections.

Another element of a spectrometer is the gas target that may be placed in the focal region. Most commercial Raman spectrometers have a gas cell that is filled with the gas sample. Appropriate windows are provided in the cell for the incident and scattered light. This arrangement is not suitable for analyzing chemically aggressive substances or molecules that easily coat glass surfaces. Careful light baffles have to be installed to suppress the light scattering from the glass as much as possible, since the scattered light covers the whole spectral range.

One embodiment may include a sample cell for collection of a breath sample. Other sample handling apparatus, adapted to handle gases (e.g. providing an effusive gas beam), liquid and solid samples, may be used. A gas sample may be heated to ensure that all water present is in vapor form, thereby avoiding solutions that would cause false concentrations to be measured, such as water condensation on the walls of the sample cell.

Optimized collection optics for the scattered light are known in the art and used in commercial Raman spectrometers. In certain embodiments an f/1 lens and a collecting mirror may be positioned at approximately +/−90° to the incident light to collect scattered light and direct it towards the dispersive analyzer.

The resonant atomic vapor filter may substantially remove a particular Raman scattered line (Stokes emission) without attenuating another spectrally proximate Raman line. In certain embodiments a filter includes a glass cell filled with, for example, a monatomic vapor, such as cesium, chosen to have an absorption resonance at a frequency equal to the frequency of the laser source minus the frequency of a particular target molecule's Raman shift, which is the frequency of a Raman line that is spectrally close to another Raman line. At an appropriate temperature, this alkali has a vapor pressure of $10^{-6}$ Torr. A 10 cm optical length of cesium vapor is sufficient to absorb and reduce the spectrally proximate light reaching an analyzer by up to 10 orders of magnitude. Other atomic vapors can be used in place of cesium, in combination with suitably chosen laser light sources. For example, another metal vapor or a noble gas may be employed as the filter medium, as well as an ionic doped glass, with a corresponding monochromatic light source chosen to produce a beam at a frequency selected to filter a particular Raman line.

The cesium absorption band can be readily adjusted by shortening the absorption cell and operating at higher temperature (to broaden the absorption band) by heating a filter. These changes maintain the optical density of a filter while raising the width of the cesium absorption line. This filtering technology is stable, simple and inexpensive. Similarly, in an embodiment where the resonant atomic vapor filter is an ionic doped glass or crystal, the width of the absorption band may be controlled by, for example, controlling the pressure applied to the glass or crystal.

The Raman scattered light is composed of a series of spectral lines which are shifted from the incident frequency generated by the laser diode arrays. Their spectral positions and their intensities provide the information sought which can be analyzed to determine the concentration of each targeted component, particularly $^{13}CO_2$ or $^{15}NO$.

Due to the use of ultra monochromatic diode laser arrays and removal of a closely spaced spectral line by atomic absorption, embodiments of this invention can provide spectral resolutions of 0.02 cm$^{-1}$. This permits identification of a molecular species that are spectrally close to others because the spectral lines may be resolved without overlap. In certain embodiments, the methods and apparatus permit resolution between compounds, which differ only in one mass unit, for example $^{12}CO_2$ and $^{13}CO_2$.

As outlined above, the methods and apparatus described will provide improved methods of testing biological, mechanical, chemical, and similar processes. Due to the use of laser diodes, the scattered light will consist of a series of spectral lines, which are very narrow, with the target spectral lines being closely spaced. Since, in one embodiment, the lasers operate at the $D_1$ transition of cesium plus the frequency of Raman shift, a cesium absorption cell in front of the spectrometer will substantially eliminate one of at least two spectrally close Raman lines. The apparatus and methods may be embodied in an inexpensive and commercially practical apparatus, avoids the use of radioactivity, and permits detection of isotopically labeled products derived from an isotopically labeled substrate.

While the above discussions have focused primarily on analysis of a gas, particularly breath, this is not a fundamental limitation. The instrument and methods can analyze the spectra solutions and from surfaces as well, with properly prepared and positioned samples, and appropriate optical elements. In any event, the atomic vapor filter and corresponding tuned light source may be used to eliminate a closely spaced spectral line and provide for resolution of Raman lines for diagnostic and testing purposes. The line width of the absorber can be adjusted to the line to be eliminated by suitable pressure broadening of the absorber resonance line. The methods and apparatus may be well suited for liquid analysis applications including analysis of blood, urine, effluent from a mechanical or chemical process and other liquids.

Isotopes

Isotopes are different forms of the same element having the same atomic number but different atomic weights. In certain embodiments the isotope used as a label is $^{13}C$. Carbon-13 is a stable isotope with a natural abundance around 1%. Substrates may be labeled with other isotopes that include stable and radioactive isotopes. Stable isotopes include but are not limited to nitrogen 15 ($^{15}N$), and oxygen 17 and 18 ($^{17}O$ and $^{18}O$), and other stable isotopes.

Substrates

Many isotopically labeled substrates, including $^{13}C$, $^{15}N$, $^{18}O$, and other isotopically labeled molecules can be employed in embodiments of the invention. Substrates that can be incorporated into embodiments of the invention include, but are not limited to $^{13}C$ labeled urea, citric acid, triglycerides, aminopyrin, octanoic acid, sodium octanoate, triolein, methacetin, caffeine citrate, lactose, galactose, sodium acetate, cholesteryl-3 octanoate, and other carbon containing substrates that when metabolized produce $^{13}CO_2$.

Samples

Sources of samples include but are not limited to exhaled breath, urine, saliva, blood, cerebrospinal fluid, tissue biopsy, and sampling of other bodily tissue or fluid. Other samples that may be analyzed by the embodied methods include, but is not limited to engine emissions; air, water, and soil samples; and the like.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method comprising detecting an isotopically labeled product of an isotypically labeled substrate by Raman spectroscopy.

2. The method of claim 1, wherein the isotopically labeled product is $^{13}C_2$.

3. The method of claim 1, wherein the isotopically labeled product and the isotopically labeled substrate are based on a compound having elements selected from a group consisting of carbon, nitrogen and hydrogen.

4. The method of claim 1, wherein Raman spectroscopy comprises utilizing an atomic vapor filter to detect the isotopically labeled product.

5. The method of claim 4, wherein the atomic vapor filter is a cesium vapor filter.

6. A Raman spectrometer comprising:
an atomic vapor filter to receive Raman scattered light; and
a laser light source to direct light on a target module to produce the Raman scattered light, wherein the frequency of the laser light source is tuned to the sum of the absorption frequency of the atomic vapor filter and a Raman shift of the target molecule;
wherein the atomic vapor filter is an alkali vapor filter, the alkali vapor filter being a cesium vapor filter.

7. The Raman spectrometer of claim 6, wherein the laser source is tuned to 12,574 $cm^{-1}$.

8. The Raman spectrometer of claim 6, wherein the target molecule includes elements selected from a group consisting of carbon, nitrogen and hydrogen.

9. A system comprising:
a Raman spectrometer that comprises,
a laser light source;
a gaseous cell to receive a gaseous compound, wherein the laser light source is to generate a laser light to pass through the gaseous compound;
an achromat to collect Raman scattered light at a focal point of the gaseous cell; and
an atomic vapor filter having an absorption frequency, the atomic vapor filter to receive the collected light, wherein the atomic vapor filter is to selectively absorb an isotope of the gaseous compound based on a frequency of the collected light; and
a data processing system to generate an isotope ratio of the gaseous compound based on intensities of the collected light passing through the atomic vapor filter at different frequencies of the laser light.

10. The system of claim 9, wherein the atomic vapor filter is an alkali vapor filter.

11. The system of claim 10, wherein the alkali vapor filter is a cesium vapor filter.

12. The system of claim 9, wherein the laser source is tuned to 12,574 $cm^{-1}$.

13. The system of claim 9, wherein the gaseous compound has elements selected from a group consisting of carbon, nitrogen and hydrogen.

14. A method comprising:
determining an intensity of a Raman scattered light at a first laser frequency passed through a gaseous compound, that is transmitted through an atomic vapor filter, the Raman scattered light having a number of spectral lines;
determining the intensity of the Raman scattered light at the second laser frequency passed through the gaseous compound, wherein the atomic vapor filter absorbs one of the spectral lines at the second laser frequency; and
generating an isotope ratio for the gaseous compound based on the intensity of the Raman scattered light at the first laser frequency and the intensity of the Raman scattered light at the second laser frequency.

15. The method of claim 14, wherein the atomic vapor filter comprises an alkali vapor filter.

16. The method of claim 15, wherein the alkali vapor filter comprises a cesium vapor filter.

17. The method of claim 14, wherein the gaseous compound has elements selected from a group consisting of carbon, nitrogen and hydrogen.

18. A machine-readable medium that provides instructions, which when executed by a machine, cause said machine to perform operations comprising:
determining an intensity of a Raman scattered light at a first laser frequency passed through a gaseous compound, that is transmitted through an atomic vapor filter, the Raman scattered light having a number of spectral lines;
determining the intensity of the Raman scattered light at the second laser frequency passed through the gaseous compound, wherein the atomic vapor filter absorbs one of the spectral lines at the second laser frequency; and
generating an isotope ratio for the gaseous compound based on the intensity of the Raman scattered light at the first laser frequency and the intensity of the Raman scattered light at the second laser frequency.

19. The machine-readable medium of claim 18, wherein the atomic vapor filter comprises an alkali vapor filter.

20. The machine-readable medium of claim 19, wherein the alkali vapor filter comprises a cesium vapor filter.

21. The machine-readable medium of claim 18, wherein the gaseous compound has elements selected from a group consisting of carbon, nitrogen and hydrogen.

22. A spectrometric method comprising:
absorbing a first spectral signal by an atomic vapor filter;
wherein the first spectral signal is proximate to a second spectral signal; and
wherein the absorption by the atomic vapor filter is of a compound having elements selected from a group consisting of carbon, nitrogen and hydrogen.

23. The method of claim 22, wherein the atomic vapor filter is an alkali vapor filter.

24. The method of claim 22, wherein the alkali vapor filter is a cesium vapor filter.

25. The method of claim 22, wherein the first spectral signal is a 1388.2 $cm^{-1}$ Raman shifted line of $^{12}CO_2$.

26. The method of claim 22, wherein the second spectral signal is a 1370.02 $cm^{-1}$ Raman shifted line of $^{-CO}{}_2$.

27. A spectrometric method comprising:
absorbing a first spectral signal by an atomic vapor filter;
wherein the first spectral signal is proximate to a second spectral signal; and
wherein the atomic vapor filter is an alkali vapor filter, the alkali vapor filter being a cesium vapor filter.

28. The method of claim 27, wherein the first spectral signal is a 1388.2 $cm^{-1}$ Raman shifted line of $^{12}CO_2$.

29. The method of claim 27, wherein the second spectral signal is a 1370.02 $cm^{-1}$ Raman shifted line of $^{13}CO_2$.

* * * * *